(12) United States Patent
Charrier (10) Patent No.: US 7,517,653 B2
(45) Date of Patent: Apr. 14, 2009

(54) IMMUNOLOGICAL TEST AND DIAGNOSTIC KIT FOR PROSTATE ADENOCARCINOMA

(75) Inventor: Jean-Philippe Charrier, Ecully (FR)

(73) Assignee: Biomerieux S.A., Marcy l'Etoile (FR)

( * ) Notice: Subject to any disclaimer, the term of this patent is extended or adjusted under 35 U.S.C. 154(b) by 241 days.

(21) Appl. No.: 10/311,014

(22) PCT Filed: Jun. 12, 2001

(86) PCT No.: PCT/FR01/01815

§ 371 (c)(1),
(2), (4) Date: Dec. 12, 2002

(87) PCT Pub. No.: WO01/96876

PCT Pub. Date: Dec. 20, 2001

(65) Prior Publication Data

US 2004/0038321 A1   Feb. 26, 2004

(30) Foreign Application Priority Data

Jun. 13, 2000   (FR) ................................. 00 07476

(51) Int. Cl.
*G01N 33/53* (2006.01)
(52) U.S. Cl. ....................................................... 435/7.1
(58) Field of Classification Search ................... 435/7.1
See application file for complete search history.

(56) References Cited

FOREIGN PATENT DOCUMENTS

| | | |
|---|---|---|
| DE | 43 22 342 | 2/1995 |
| FR | 2 780 791 | 1/2000 |
| WO | WO 92/01936 | * 2/1992 |
| WO | WO 95/18381 | 7/1995 |
| WO | WO 99/10745 | 3/1999 |
| WO | WO 99/61914 | 12/1999 |

OTHER PUBLICATIONS

Appewhite et al. (Cancer Control, Mar.-Apr. 2001, 8(2):141-150).*
Lilja et al (WO 92/01936; Feb. 6, 1992).*
Applewhite et al (Cancer Control, Mar.-Apr. 2001, 8(2):141-150).*
Tockman et al (Cancer Res., 1992, 52:2711s-2718s).*

* cited by examiner

*Primary Examiner*—Sean E Aeder
(74) *Attorney, Agent, or Firm*—Daniel A. Monaco; Drinker Biddle & Reath LLP

(57) ABSTRACT

This invention concerns a test method for the purposes of diagnosis, prognosis or therapeutic monitoring in male patients with adenocarcinoma of the prostate or benign prostatic hyperplasia, which does not require a biopsy of prostate tissue, and which exploits the combination of at least one tissue-specific marker and at least one marker for inflammation in order to arrive at a diagnosis.

The invention also concerns a process using such a method, an immunological test to implement such a process, and a diagnostic kit.

The invention is applied to the diagnosis of adenocarcinoma of the prostate and benign prostatic hyperplasia.

6 Claims, 4 Drawing Sheets

IMMUNOLOGICAL TEST AND DIAGNOSTIC KIT FOR PROSTATE ADENOCARCINOMA

This invention concerns a screening or diagnostic method for the detection of prostate cancer (i.e. adenocarcinoma of the prostate, usually abbreviated to PCa) and benign prostatic hyperplasia (abbreviated to BPH) in patients, a method which does not involve the taking of a biopsy. More generally, the invention concerns a test method for the purposes of diagnosis, prognosis or therapeutic monitoring of cancer in human patients.

By diagnosis, it is meant that the marker reveals whether or not the patient is suffering from a certain disease. By prognosis, it is meant that the marker reveals the seriousness of the disease. The prognosis can guide the therapeutic strategy. Finally, by therapeutic monitoring, it is meant that the marker can be used to follow the efficacy of treatment. If the chosen treatment strategy is failing (as revealed by the marker), the patient can be offered an alternative.

Prostate-specific antigen (PSA) is synthesized by epithelial cells of the human prostate gland, probably in the form of an inactive zymogen (Lundwall et al. FEBS LeH 1987) and is secreted in the seminal fluid in an active form (Lilja, J. Clin Invest 1985). The biological activity of PSA in seminal fluid consists of controlled proteolysis of the most abundant proteins secreted by the seminal vesicles (Lilja, J. Clin Invest 1985; Lilja et al. J. Clin Invest 1987; Mc Gee et al. Biol. Reprod. 1988).

PSA is the most important marker for prostate cancer, a disease which eventually affects one man in six in the developed world. This protease which belongs to the kallikrein family is mainly secreted by the prostatic epithelium. Its normal concentration in seminal fluid is between 0.5 and 5 mg/ml; in the serum, its normal concentration is one million times lower. Thus, the normal serum concentration of PSA is below 2.5 ng/ml. However, its concentration in the blood can be much higher in certain circumstances, notably in patients with prostate cancer; its levels may also be elevated—although usually to a lesser extent—in benign conditions such as benign prostatic hyperplasia (BPH) and acute prostatitis.

The amino acid sequence of PSA has been determined: it is a glycoprotein containing 237 amino acids ("Molecular cloning of human prostate specific antigen cDNA". Lundwall A., Lilja H., 1987. *FEBS Lett* 214: 317-322).

However, the significant overlap between different pathologies gives rise to a serious lack of both sensitivity and specificity. For this reason, while 30 to 45% of cases in which the malignancy is still confined to the gland (i.e. at an early stage and therefore possibly curable) are missed on the basis of the routinely applied normal limit of 4 ng/ml, fully three out of four subjects tested are mistakenly suspected of having cancer.

It has been shown recently that in serum, PSA binds protease inhibitors such as $\alpha$-1-antichymostrypsin (ACT), and that the ratio of free PSA to total PSA might be a more specific diagnostic indicator.

ACT is 68,000 Dalton glycoprotein found in the plasma: its sequence is known (Chandra T., Stackhouse R., Kidd V. J., Robson K. J., Woo S. L.; Biochemistry 1983 Oct. 25; 22 (22): 5055-5061; Sequence homology between human $\alpha$-1-antichymotrypsin, $\alpha$-1-antitrypsin, and antithrombin III). It belongs to the serpine family and inhibits a number of different serine proteases including $\alpha$-1-chymotrypsin and PSA. Its concentration in the blood rises in response to cell damage due to physical injury, surgery or infection and it is one of the proteins associated with inflammation. The usefulness of assaying ACT has been reported for a number of conditions, including rheumatoid arthritis, Alzheimer's disease, Hodgkin's disease and stomach cancer. However, the value of assaying serum ACT has not hitherto been demonstrated with respect to the diagnosis of prostate cancer. Even those skilled in the art have been discouraged by the background art which puts the emphasis on simple PSA concentration ratios.

The background art shows that methods exist for diagnosing the development of prostate cancer in patients. Thus, patent application WO-A-97/12245 claims a method which is able to diagnose adencarcinoma without any need for a biopsy. This method involves measuring the total amount of PSA present in either patient's blood or serum. If the result falls between 2.5 and 20 ng/ml, the concentration of free PSA is also measured and then the ratio of free PSA to total PSA is calculated. If this ratio is below 7%, a diagnosis of adenocarcinoma of the prostate is to be considered.

However, the cut-off point of 7% for a diagnosis of prostate cancer is controversial as discussed by Lein et al. in an article entitled "Relation of free PSA/total PSA in serum for differentiating between patients with prostatic cancer and benign prostate hyperplasia: which cutoff should be used?" In this article published in Cancer Investigation, 16(1), 45-49, 1998, it was shown that it is not always easy to make the distinction between malignancy (adenocarcinoma of the prostate) and benign prostatic hyperplasia based on this ratio.

Moreover, in their article entitled "Prostate Cancer Detection in Men With Serum PSA Concentrations of 2.6 to 4.0 ng/ml and Benign Prostate Examination", published in JAMA on May 14 1997-Vol 277, No,18, Catalona et al. show that concentrations of below 4 ng/ml need to be taken into account when it comes to early screening for prostate cancer.

In Patent Application WO-A-00/02052, the Applicant described a method to overcome the poor reliability of test results corresponding to total PSA concentrations superior to 2 ng/ml. To this end, the different molecular forms of PSA in the serum of patients with either cancer or BPH were analyzed by two-dimensional electrophoresis and then visualized using chemoluminescence: this gave a full picture of all the different forms, i.e. free, complexed and cleaved PSA.

This showed that the profile in cancer patients tended to be relatively homogeneous whereas in BPH, there was a higher proportion of cleaved PSA and there were a few more basic spots.

Therefore, it has been shown that an increased ratio of Free PSA to Total PSA could in some cases be due either to the presence of inactive, cleaved PSA which cannot bind ACT, or to the free PSA being slightly more basic (which could correspond to the inactive zymogen).

In another Patent Application (FR00/04591), the Applicant described the development of immunological tests to implement the diagnostic method described in WO-A-00/02052.

However, using antibodies specifically directed against either cleaved or native PSA is far more difficult because, apart from the two described in Patent Application FR00/04591, very few are on the market or available. This is not the case for other parameters such as Total PSA (Free+Complexed), PSA-ACT and Total Free PSA (i.e. Cleaved+Native) which are relatively simple parameters, well known in the background art. The ratio according to this invention is derived from measurements of parameters which are already well established in the prior art so the test can be easily carried out in most medical test laboratories.

Thus for example, PSA complexed with ACT is assayed using the antibody described in Patent Application WO-A-98/22509.

Total PSA is assayed using either the antibody described by H. Nagasaki et al. (1999), Clin. Chem. 45: 4486-4496, or that sold by Scripps Laboratories (San Diego, USA).

For example, Free PSA could be assayed using either the antibodies described in Patent Application WO 92/01936, or the monoclonal antibodies sold by Chagaï (Japan).

Finally, ACT could for example be assayed using the antibodies described in the article by Sprecchia G., Petroboni V., Fratino P., and Dander B. entitled "Introduction of antichymotrypsin antibodies: their identification and interference with tryptic activity, Boll. Soc. Ital. Biol. Sper. 1970 Feb. 15; 46(3): 111-4. Other antibodies which can be used to assay ACT are available from Dako (Trappes, France) and Valbiotech (Paris, France). For example, an assay method has been described by Calvin J and Price C. P., Measurement of serum alpha-1-antichymotrypsin by immunoturbidimetry, Ann. Clin. Biochem. 1986; 23; 206-209.

Therefore, the method consists in assaying Free PSA, Total PSA (or alternatively PSA-ACT) and ACT in some biological fluid, and then deriving the following ratio:

$$\frac{[ACT] \times [\text{Total } PSA]^2}{[\text{Free } PSA]} \text{ which is expressed in } (\mu g/ml)^2.$$

The patient is diagnosed as having adenocarcinoma of the prostate if this ratio is greater than a first value, and as having benign prostatic hyperplasia if the ratio is below a second value.

Moreover, compared with the ratio of Free PSA to Total PSA which is well known in prior art, the ratio according to this invention discriminates significantly more effectively between benign prostatic hyperplasia and adenocarcinoma of the prostate. In consequence, the invention will considerably reduce the number of biopsies that will have to be taken to confirm a diagnosis of malignancy. It will therefore reduce both health care costs and the inconvenience to patients which necessarily accompanies the taking of a biopsy.

Finally, this ratio sums up the effect of three different parameters in a single value: the ratio of Free PSA to Total PSA, the level of Total PSA, and the level of ACT. As a result, the clinician needs only analyze a single figure which makes interpretation easier. He/she will no longer have to integrate the ratio of Free PSA to Total PSA with the absolute level of Total PSA, as was the case up till now. Moreover, the ratio according to this invention increases in prostate cancer whereas it is low in benign prostatic hyperplasia. This result therefore makes it easy to define the stage and seriousness of prostate cancer.

To this effect, this invention concerns a test method for the purposes of diagnosis, prognosis or therapeutic monitoring in male patients with adenocarcinoma of the prostate or benign prostatic hyperplasia, which does not require a biopsy of prostate tissue, and which exploits the combination of at least one tissue-specific marker and at least one marker for inflammation in order to arrive at a diagnosis.

This method consists in using PSA as the tissue-specific marker, and ACT as the marker for inflammation.

According to a preferred embodiment, the tissue-specific marker is constituted by one of the following, and preferably at least two of them in the form of a ratio:
[Free PSA],
[Total PSA], and
[PSA-ACT].

According to another preferred embodiment, the marker for inflammation is the following: [ACT].

In all the examples given and according to a first method, the ratio based on a combination of at least one tissue-specific marker and at least one marker for inflammation is as follows:

$$\frac{[ACT] \times [\text{Total } PSA]^2}{[\text{Free } PSA]}.$$

According to this first method: when the ratio is greater than 30 and preferably greater than 50 $(\mu g/ml)^2$, a diagnosis of adenocarcinoma of the prostate is made; and when the ratio is below 16.5 and preferably below 12 $(\mu g/ml)^2$, the diagnosis is one of benign prostatic hyperplasia.

In all the examples given and according to a second method, the ratio based on a combination of at least one tissue-specific marker and at least one marker for inflammation is as follows:

$$\frac{[ACT] \times [PSA - ACT] \times [\text{Total } PSA]^2}{[\text{Free } PSA]}.$$

According to this second method: when the ratio is greater than 23 and preferably greater than 45 $(\mu g/ml)^2$, a diagnosis of adenocarcinoma of the prostate is made; and when the ratio is below 13.5 and preferably below 9 $(\mu g/ml)^2$, the diagnosis is one of benign prostatic hyperplasia.

In all the examples given and according to a third method, the ratio based on a combination of at least one tissue-specific marker and at least one marker for inflammation is either as follows or the inverse ratio:

$$\frac{[ACT] \times [PSA - ACT]^2}{[\text{Free } PSA]}.$$

According to this third method: when the ratio is greater than 17 and preferably greater than 40 $(\mu g/ml)^2$, a diagnosis of adenocarcinoma of the prostate is made; and when the ratio is below 12 and preferably below 7 $(\mu g/ml)^2$, the diagnosis is one of benign prostatic hyperplasia.

In a more general way, the invention concerns a test method for the purposes of diagnosis, prognosis or therapeutic monitoring in any human patient with cancer, which exploits the combination of at least one tissue-specific marker and at least one marker for inflammation in order to arrive at a diagnosis This invention also concerns a process using a method as described above, which consists in:
 measuring the parameters which enter into the ratio to be used,
 deriving the value of the ratio,
 comparing the result with reference values, and
 establishing a diagnosis of either adenocarcinoma of the prostate or benign prostatic hyperplasia, or alternatively defining the result as borderline and proceeding to further exploratory procedures such as biopsy analysis, a digital rectal examination or a transrectal ultrasound examination.

The invention also concerns an immunological test to implement a process as described above, in which are used:
 specific antibodies directed against one and preferably at least two of the following antigens: Free PSA, Total PSA, and PSA-ACT, as the tissue-specific marker,
 ACT as the marker for inflammation.

Finally, the invention concerns a kit for the purposes of diagnosis, prognosis or therapeutic monitoring of adenocarcinoma of the prostate in a patient suspected of having said type of adenocarcinoma, or for differentiating between benign prostatic hyperplasia and adenocarcinoma of the prostate in a subject suspected of having one of these two diseases, said kit comprising:

means for assaying one of the following parameters, and preferably at least two of them: Free PSA, Total PSA, and PSA-ACT, as the tissue-specific marker, and means for assaying ACT as the marker for inflammation.

Preferably these means are antibodies.

The accompanying drawings are given by way of example and are not to be taken as limiting in any way. They are designed to make the invention easier to understand.

Finally.

The usefulness of assaying Total PSA and determining the ratio of Free PSA to Total PSA is well characterized in the background art, as explained above. In contrast, the usefulness of simultaneously assaying ACT has never been demonstrated when it comes to either diagnosis or differentiating between benign prostatic hyperplasia and adenocarcinoma of the prostate.

A—Experiments Already Carried Out

Free PSA was assayed using the Vidas FPSA kit (BioMérieux) following the manufacturer's recommendations.

Total PSA was assayed using the Vidas TPSA kit (BioMérieux) following the manufacturer's recommendations.

ACT was assayed by immunoturbidimetry using a method adapted from J. Calvin et C. P. Price ("Mesure of serum α1-antichymotrypsin by immunoturbidimetry" Ann, Clin, Biochem, 1986; 23: 206-209) with the following protocol:

Prepare Buffer A: 5 mM sodium phosphate, 130 mM NaCl, 64 g/l polyethylene glycol 6000, pH=7,2.

Prepare Solution B: dilute the anti-ACT antibody (Dako, Reference A022) 16-fold in Buffer A.

Prepare a set of ACT standards by diluting purified ACT (Scipac, Reference P159-5) in Buffer A.

Dilute test serum samples 10-fold in Buffer A.

Leave serum samples and ACT standards at room temperature for 15 minutes.

Centrifuge serum samples and ACT standards for 10 minutes at 2000 g at a temperature of 15° C.

Measure the extent of complex formation between the anti-ACT antibody and the ACT by following the increase in optical density (OD) at 340 nm and 700 nm on a Hitachi 704 machine. The machine is programmed to dilute 18 µl of the test sample or standard in Buffer A to a volume of 141 µl, make up a serum blank, add 141 µl of Solution B to each, and read the final OD of the solution.

Draw up a standard curve with the concentration of each ACT standard plotted against the corresponding OD reading.

Work out the ACT concentration in each of the test samples by reading the value corresponding to the OD reading from the standard curve.

Calculate the following ratio:

$$\frac{[ACT] \times [\text{Total } PSA]^2}{[\text{Free } PSA]} \; (\text{in } \mu g/ml)^2$$

A diagnosis of prostate cancer is made if the above ratio is greater than 30 $(\mu g/ml)^2$.

A diagnosis of benign prostatic hyperplasia is made if the above ratio is less than 16.5 $(\mu g/ml)^2$.

The ratio according to this invention was used in an experiment on samples taken from twenty-eight (28) patients with BPH and thirty-eight (38) with prostate cancer. The results are presented in Table 1 below.

TABLE 1

Analysis of 28 patients with BPH and 38 with PCa

| Patient | Disease | Total PSA (ng/ml) | Free PSA (ng/ml) | ACT (µg/ml) | $\frac{[\text{Free PSA}]}{[\text{Total PSA}]}$ (%) | $\frac{[ACT] \times [\text{Total PSA}]^2}{[\text{Free PSA}]}$ |
|---|---|---|---|---|---|---|
| 1 | BPH | 1.04 | 0.20 | 861.40 | 19.23 | 4.66 |
| 2 | BPH | 1.47 | 0.35 | 875.20 | 23.81 | 5.40 |
| 3 | BPH | 3.01 | 0.32 | 879.00 | 10.63 | 24.89 |
| 4 | BPH | 8.27 | 3.50 | 616.30 | 42.32 | 12.04 |
| 5 | BPH | 7.50 | 0.83 | 926.30 | 11.07 | 62.78 |
| 6 | BPH | 3.90 | 0.87 | 796.80 | 22.31 | 13.93 |
| 7 | BPH | 16 | 2.24 | 661.50 | 14.00 | 75.60 |
| 8 | BPH | 9.13 | 2.84 | 946.00 | 31.11 | 27.77 |
| 9 | BPH | 6.22 | 1.15 | 634.90 | 18.49 | 21.36 |
| 10 | BPH | 4.01 | 0.52 | 317.50 | 12.97 | 9.82 |
| 11 | BPH | 5.8 | 1.86 | 465.00 | 32.07 | 8.41 |
| 12 | BPH | 5.03 | 0.46 | 279.10 | 9.15 | 15.35 |
| 13 | BPH | 4.55 | 1.01 | 518.50 | 22.20 | 10.63 |
| 14 | BPH | 4.85 | 0.41 | 578.70 | 8.45 | 33.20 |

TABLE 1-continued

Analysis of 28 patients with BPH and 38 with PCa

| Patient | Disease | Total PSA (ng/ml) | Free PSA (ng/ml) | ACT (μg/ml) | $\frac{[\text{Free PSA}]}{[\text{Total PSA}]}$ (%) | $\frac{[\text{ACT}] \times [\text{Total PSA}]^2}{[\text{Free PSA}]}$ |
|---|---|---|---|---|---|---|
| 15 | BPH | 4.17 | 0.71 | 969.10 | 17.03 | 23.73 |
| 16 | BPH | 4.52 | 1.05 | 568.30 | 23.23 | 11.06 |
| 17 | BPH | 6.81 | 1.02 | 472.70 | 14.98 | 21.49 |
| 18 | BPH | 4.16 | 0.73 | 877.30 | 17.55 | 20.80 |
| 19 | BPH | 5.55 | 1.00 | 669.40 | 18.02 | 20.62 |
| 20 | BPH | 4.6 | 0.79 | 599.80 | 17.17 | 16.07 |
| 21 | BPH | 4.23 | 0.44 | 458.40 | 10.40 | 18.64 |
| 22 | BPH | 6.71 | 1.56 | 536.60 | 23.25 | 15.49 |
| 23 | BPH | 7.67 | 2.57 | 911.70 | 33.51 | 20.87 |
| 24 | BPH | 5.12 | 0.54 | 559.60 | 10.55 | 27.17 |
| 25 | BPH | 4.18 | 2.28 | 804.00 | 54.55 | 6.16 |
| 26 | BPH | 5.01 | 1.17 | 586.90 | 23.35 | 12.59 |
| 27 | BPH | 7.21 | 1.43 | 585.10 | 19.83 | 21.27 |
| 28 | BPH | 5.24 | 0.72 | 595.70 | 13.74 | 22.72 |
| 29 | PCa | 2.31 | 0.31 | 976.10 | 13.42 | 16.80 |
| 30 | PCa | 12.47 | 0.81 | 983.80 | 6.50 | 188.87 |
| 31 | PCa | 46.46 | 3.43 | 1165.30 | 7.38 | 733.33 |
| 32 | PCa | 98.82 | 7.68 | 852.70 | 7.77 | 1084.24 |
| 33 | PCa | 58.82 | 6.84 | 1096.00 | 11.63 | 554.38 |
| 34 | PCa | 17.49 | 1.09 | 757.00 | 6.23 | 212.45 |
| 35 | PCa | 31.01 | 2.58 | 1453.70 | 8.32 | 541.82 |
| 36 | PCa | 29.83 | 1.73 | 377.30 | 5.80 | 194.06 |
| 37 | PCa | 26.51 | 3.16 | 902.20 | 11.92 | 200.65 |
| 38 | PCa | 10.57 | 0.70 | 1059.80 | 6.62 | 169.15 |
| 39 | PCa | 10.55 | 2.09 | 2000.00 | 19.81 | 106.51 |
| 40 | PCa | 11.43 | 0.89 | 1496.50 | 7.79 | 219.67 |
| 41 | PCa | 40.39 | 10.00 | 668.10 | 24.76 | 108.99 |
| 42 | PCa | 7.9 | 1.79 | 1549.00 | 22.66 | 54.01 |
| 43 | PCa | 6.77 | 0.61 | 1311.70 | 9.01 | 98.56 |
| 44 | PCa | 5.56 | 0.86 | 835.20 | 15.47 | 30.02 |
| 45 | PCa | 10.84 | 2.56 | 662.70 | 23.62 | 30.42 |
| 46 | PCa | 713.00 | 104.00 | 1383.50 | 14.59 | 6762.77 |
| 47 | PCa | 11.00 | 1.21 | 703.00 | 11.00 | 70.30 |
| 48 | PCa | 10.5 | 0.84 | 801.30 | 8.00 | 105.17 |
| 49 | PCa | 9 | 2.61 | 1138.80 | 29.00 | 35.34 |
| 50 | PCa | 5.4 | 0.38 | 722.30 | 7.00 | 55.72 |
| 51 | PCa | 4000 | 567.00 | 1026.50 | 14.18 | 28966.49 |
| 52 | PCa | 9.5 | 0.34 | 734.40 | 3.58 | 194.94 |
| 53 | PCa | 9.58 | 1.23 | 853.30 | 12.84 | 63.67 |
| 54 | PCa | 7.07 | 1.24 | 606.20 | 17.54 | 24.44 |
| 55 | PCa | 4.09 | 0.70 | 907.90 | 17.11 | 21.70 |
| 56 | PCa | 6.81 | 0.92 | 762.50 | 13.51 | 38.44 |
| 57 | PCa | 18.41 | 1.64 | 1836.80 | 8.91 | 379.60 |
| 58 | PCa | 8.09 | 1.00 | 707.00 | 12.36 | 46.27 |
| 59 | PCa | 20.29 | 3.15 | 2000.00 | 15.52 | 261.39 |
| 60 | PCa | 29.98 | 7.15 | 727.00 | 23.85 | 91.39 |
| 61 | PCa | 7.39 | 1.18 | 508.30 | 15.97 | 23.52 |
| 62 | PCa | 5.42 | 0.84 | 790.90 | 15.50 | 27.66 |
| 63 | PCa | 5.66 | 0.70 | 967.70 | 12.37 | 44.29 |
| 64 | PCa | 5.42 | 0.30 | 546.90 | 5.54 | 53.55 |
| 65 | PCa | 4.98 | 0.29 | 596.30 | 5.82 | 50.99 |
| 66 | PCa | 4.63 | 0.71 | 776.00 | 15.33 | 23.43 |

The data shown in Table 1 are plotted in FIGS. 1 to 4.

Figure 1:
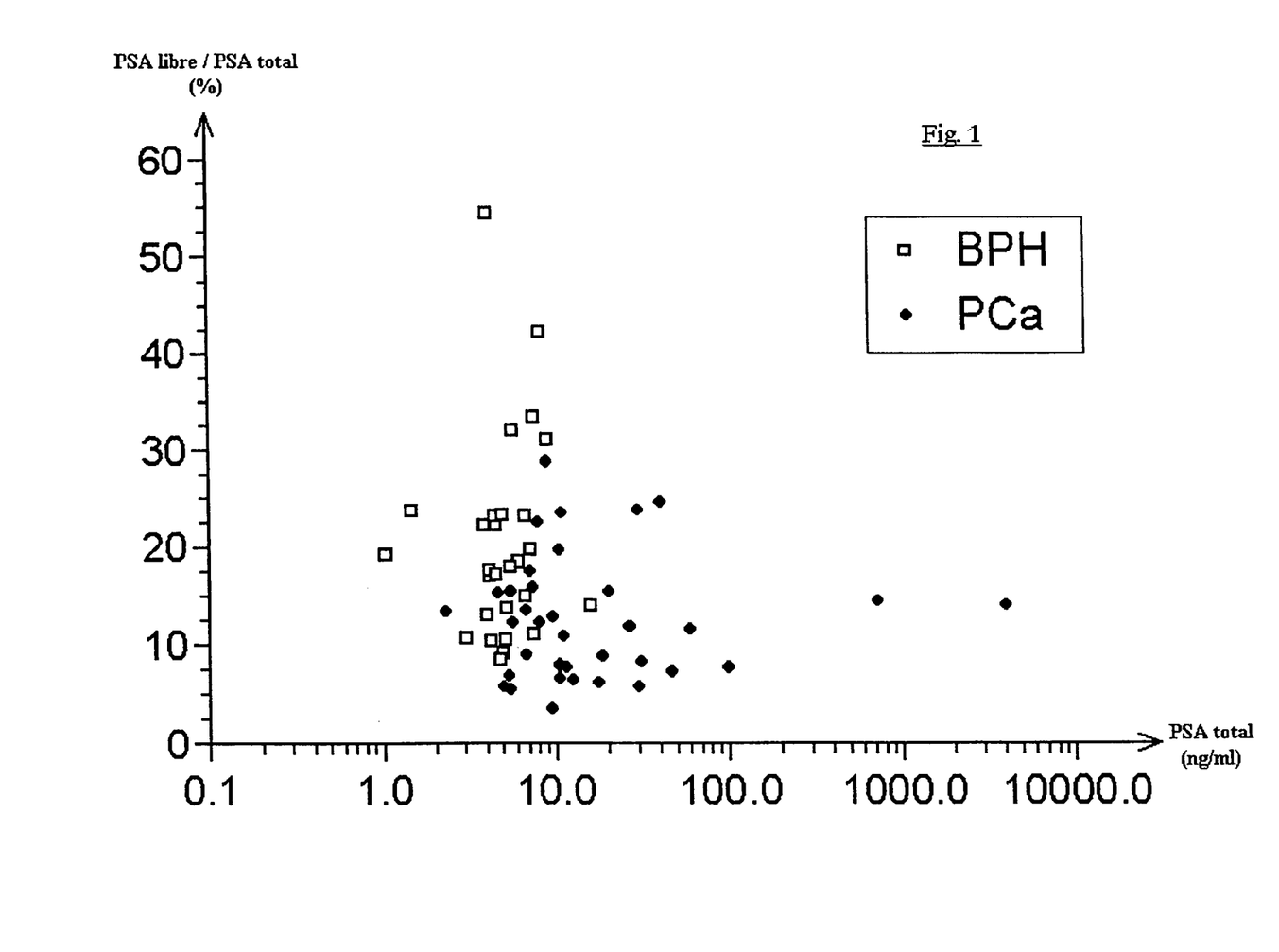
FIG. 1 is a diagram showing cases of benign prostatic hyperplasia and of adenocarcinoma of the prostate plotted in terms of Total PSA concentration (on the abscissa) versus the ratio (expressed as a percentage) of the concentration of Free PSA to that of Total PSA (on the ordinate).

FIG. 1 illustrates the resolving power of considering Total PSA in conjunction with the ratio of Free PSA to Total PSA, as used in the background art. The diagram shows that these two parameters do not correlate with one another and that comparing them gives complementary, independent information.

Thus, if a cut-off of 7% is taken (the threshold highlighted in the discussion of the background art), although it can be seen that all patients presenting a ratio of below 7% do indeed have cancer, this is by no means the case for results of between 7 and 30% in which range patients with benign prostatic hyperplasia and those with adenocarcinoma of the prostate are completely mixed. Not until the threshold of 30% is passed do all the patients have benign prostatic hyperplasia.

Therefore, there is a borderline range which entails a public health problem. The number of false negatives actually constitutes a majority since twenty-four (24) of the thirty-eight (38) patients with cancer fall in this range.

Figure 2:
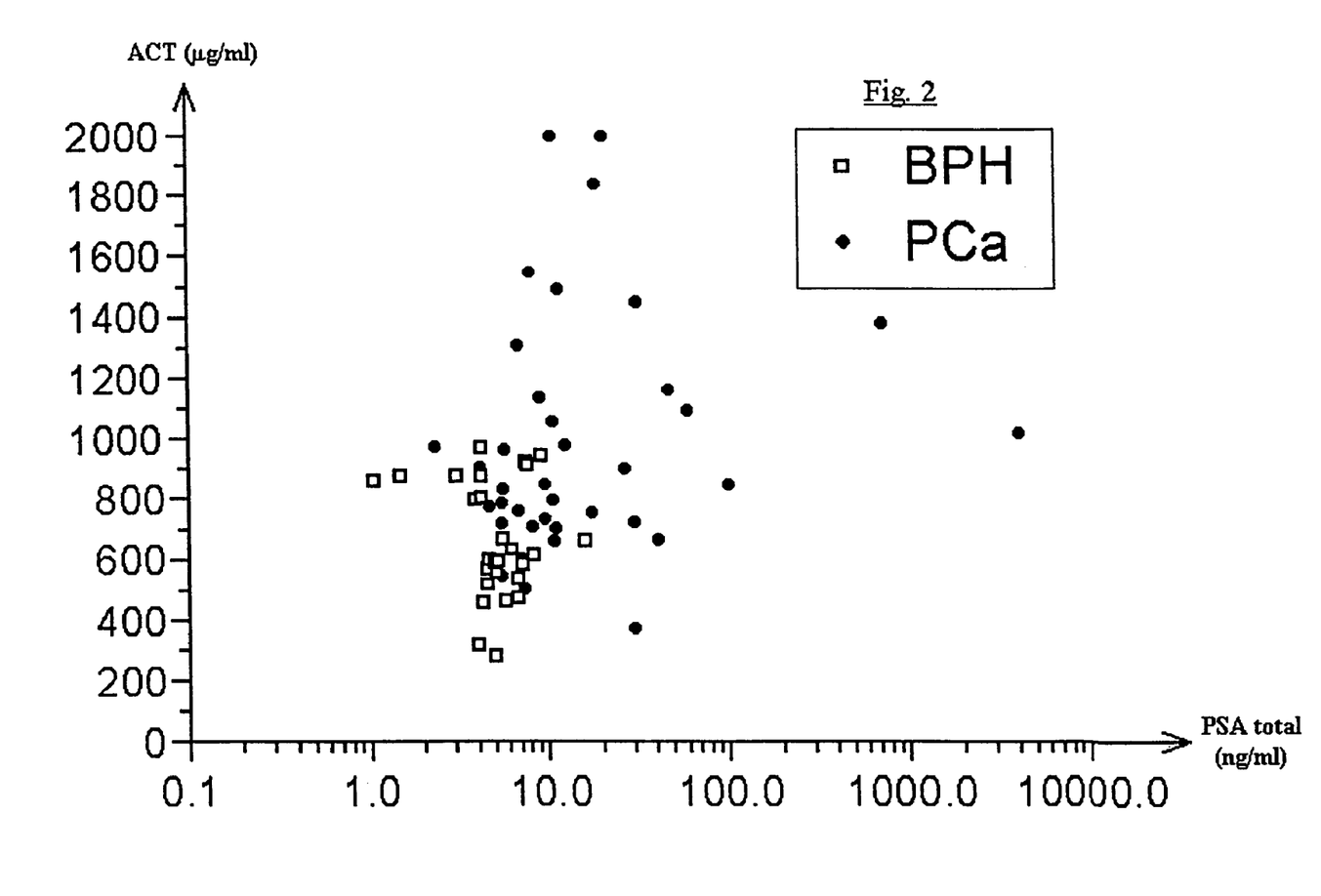
FIG. 2 is a diagram showing cases of benign prostatic hyperplasia and of adenocarcinoma of the prostate plotted in terms of Total PSA concentration (on the abscissa) versus ACT concentration (on the ordinate).

FIG. 2 illustrates the resolving power of considering ACT in conjunction with Total PSA. The diagram shows that these two parameters do not correlate with one another and that comparing them gives complementary, independent information.

Figure 3:
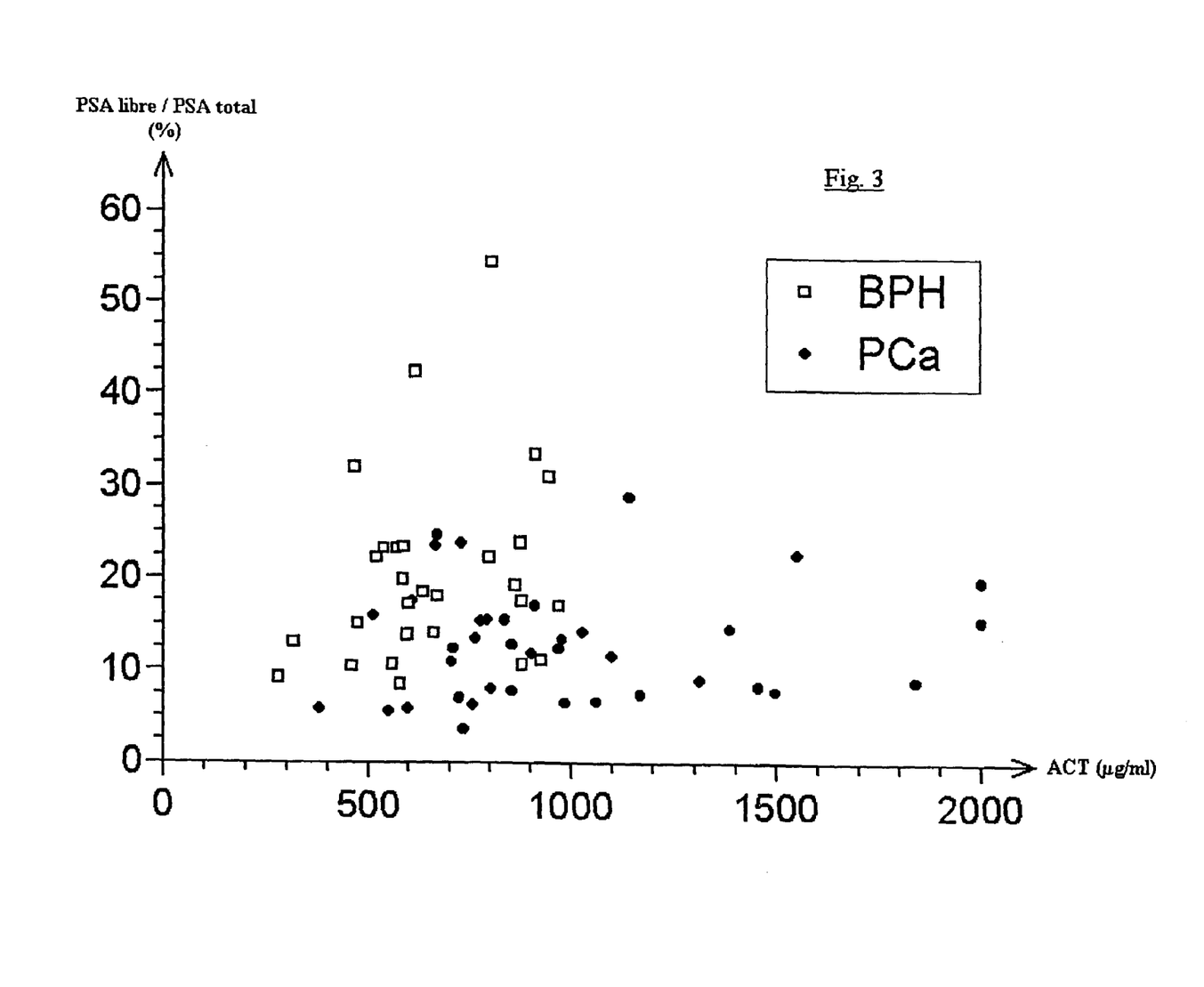
FIG. 3 is a diagram showing cases of benign prostatic hyperplasia and of adenocarcinoma of the prostate plotted in terms of ACT concentration (on the abscissa) versus the ratio (expressed as a percentage) of the concentration of Free PSA to that of Total PSA (on the ordinate).

FIG. 3 illustrates the resolving power of considering ACT in conjunction with the ratio of Free PSA to Total PSA. The diagram shows that these two parameters do not correlate with one another and that comparing them gives complementary, independent information.

It follows on therefore from the data presented in FIGS. 1 to 3 that measurements of ACT and Total PSA together with the ratio of Free PSA to Total PSA all give complementary but independent information. It is therefore either impossible to draw any conclusions from looking at these diagrams (FIGS. 2 and 3), or the results are difficult to interpret and not robust (FIG. 1).

Integrating all three of these parameters into a single value in the form of the ratio according to this invention enhances the relevance of each of these parameters (compared with the values on their own) to a surprising extent.

Figure 4:
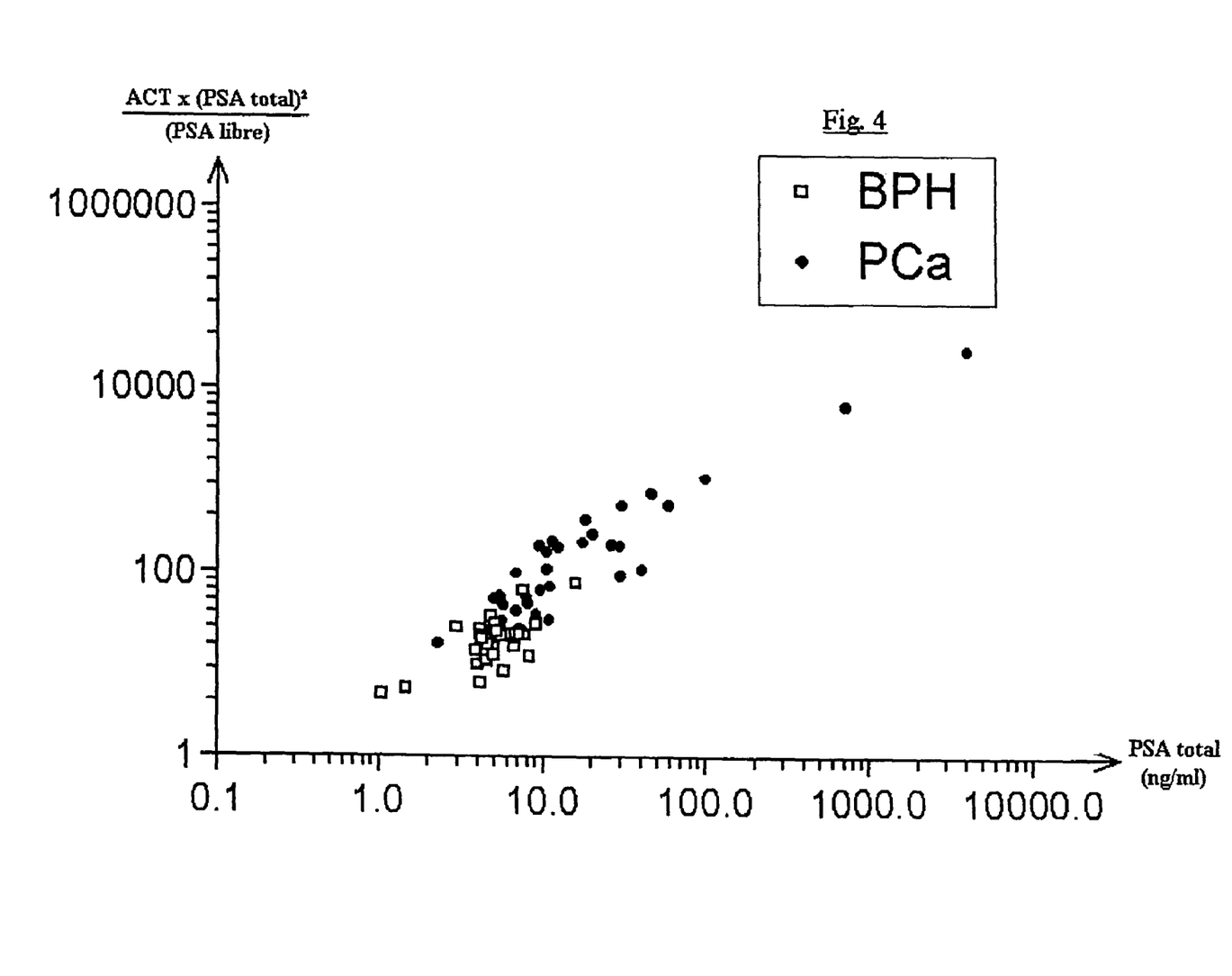
FIG. 4 is a diagram showing cases of benign prostatic hyperplasia and of adenocarcinoma of the prostate plotted in terms of Total PSA concentration (on the abscissa) versus a ratio according to the invention (on the ordinate).

FIG. 4 illustrates the resolving power of the invention characterized by the use of the ratio in $(\mu g/ml)^2$:

$$\frac{[ACT] \times [Total\ PSA]^2}{[Free\ PSA]}.$$

The Figure shows, by way of example, the close correlation between said ratio and Total PSA concentration, The four Tables 2 through 5 illustrate the advantage of the invention over the use of the ratio of Free PSA to Total PSA familiar in the background art.

TABLE 2

Resolving power of the ratio $\frac{[Free\ PSA]}{[Total\ PSA]}$ using the same thresholds as those stipulated in Patent Application WO-A-97/12245

| $\frac{[Free\ PSA]}{[Total\ PSA]}$ | ≤7% | 7 to 25% | ≥25% |
|---|---|---|---|
| PCa | 8/38 = 21.1% | 29/38 = 76.3% | 1/38 = 2.6% |
| BPH | 0/28 = 0% | 23/28 = 82.1% | 5/28 = 17.9% |

TABLE 3

Resolving power of the ratio $\frac{[Free\ PSA]}{[Total\ PSA]}$ using the previous threshold in conjunction with Thresholds for Total PSA

| $\frac{[Free\ PSA]}{[Total\ PSA]}$ | ≤7% | 7 to 25% | ≥25% |
|---|---|---|---|
| PSA total | ≥10 ng/ml | >4 but <10 ng/ml | ≤4 ng/ml |
| PCa | 24/38 = 63.2% | 12/38 = 31.6% | 2/38 = 5.3% |
| BPH | 1/28 = 3.6% | 18/28 = 64.3% | 9/28 = 32.1% |

TABLE 4

Resolving power of the ratio $\frac{[Free\ PSA]}{[Total\ PSA]}$ using thresholds optimized in a way comparable to those of the ratio $\frac{[ACT] \times [Total\ PSA]^2}{[Free\ PSA]}$

| $\frac{[Free\ PSA]}{[Total\ PSA]}$ | ≤10.4% | 10.4 to 29% | ≤29% |
|---|---|---|---|
| PCa | 15/38 = 39.5% | 22/38 = 57.9% | 0/38 = 0% |
| BPH | 2/28 = 7.1% | 21/28 = 75% | 5/28 = 17.9% |

TABLE 5

Resolving power of the ratio $\frac{[ACT] \times [Total\ PSA]^2}{[Free\ PSA]}$ using optimized thresholds

| $\frac{[ACT] \times [Total\ PSA]^2}{[Free\ PSA]}$ | ≥30 $(\mu g/ml)^2$ | 16.5 to 30 $(\mu g/ml)^2$ | ≤16.5 $(\mu g/ml)^2$ |
|---|---|---|---|
| PCa | 32/38 = 84.2% | 6/38 = 15.8% | 0/38 = 0% |
| BPH | 3/28 = 10.7% | 12/28 = 42.9% | 13/28 = 46.4% |

It can be clearly seen that, compared with the best criteria used in the background art (Table 4), the ratio proposed in this invention (Table 5) correctly diagnoses significantly more cases of both cancer (32 compared with 24) and BPH (13 compared with 9) while at the same time considerably reducing the number of borderline results (18 compared with 30).

Both methods give exactly the same number of false results, with this invention classifying three (3) cases as of adenocarcinoma of the prostate whereas subsequent biopsy analysis showed that these patients actually only had benign prostatic hyperplasia. In the case of ratios, according to the background art, two (2) cases of cancer by biopsy are in fact benign prostatic hyperplasia and one (1) is in fact an adenocarcinoma of the prostate for the background art.

Even if the number of false positives is the same, using the ratio according to the invention is safer because it did not fail to detect any patient with cancer whereas the background art would have missed two such cases.

It is important to emphasize that, in contrast to the background art (Tables 2 and 3), this invention does not mistakenly diagnose a single case of cancer as benign prostatic hyperplasia. This type of mis-diagnosis is far more dangerous than the converse one (i.e. the mistaking of benign prostatic hyperplasia for cancer) which is possible although rare with the present invention (2 out of 66 cases). In practice, a diagnosis of cancer is routinely confirmed by biopsy analysis which minimizes the risk of a definitively incorrect diagnosis of malignancy.

On the other hand, biopsies are never ordered when the diagnosis is one of benign prostatic hyperplasia. The consequence is that someone with cancer who is falsely diagnosed as having benign prostatic hyperplasia will not be given the appropriate treatment. His cancer will not be diagnosed until later, by which stage the disease will have advanced and both his chance of cure and his life expectancy will be lower.

B—Experiments Which can be Carried Out and Which Could be Carried Out

Any other assay methods for the three parameters (Free PSA, Total PSA and ACT) could be used. By way of example, we have also assayed ACT by both immunoelectrophoresis and ELISA.

The immunoelectrophoretic assay for ACT was performed according to the method of C. B. Laurell (Anal. Biochem, 1966, 15, 45-52) and by adapting the method described by J. Calvin et C. P. Price ("Mesure of serum α1-antichymotrypsin by immunoturbidimetry" Ann. Clin. Biochem, 1986; 23: 206-209). The protocol comprises the following steps:

Prepare Buffer C: 1.842 g/l acid barbital, 10.3 g/l barbital sodium, 5.8 g/l sodium acetate, pH=8,6.

Prepare Solution D: 9 g/l NaCl, 0.01% Bromophenol Blue.

Prepare Solution E: Dissolve 10 g/l agarose in Buffer C (diluted 4-fold) by heating the solution in a water bath. Allow it to cool to 55° C. Add 147 µl anti-ACT antibody (Dako, Reference A0022) for every 22 ml of the agarose solution.

Prepare Solution F: 25% ethanol 25%, 10% acetic acid, 65% distilled water.

Prepare Solution G: R-250 Coomassie Blue diluted to 1.15 g/l in Solution F.

Pour 22 ml of Solution E at a temperature of 55° C. into a 10×13 cm plate of gel bond Agarose (Pharmacia, Reference 80-1129-32). Leave to cool and set.

Punch two wells with a diameter of 2 mm near the 13 cm edge of the gel.

Introduce the gel into the immunoelectrophoresis apparatus (Gelman Science, Deluxe Electrophoresis Chamber) with wicks applied to the edges of the gel and submerged in Buffer C.

Prepare a set of ACT standards by diluting purified ACT (Scipac, Reference P159-5) in Buffer D.

Dilute the serum samples 10-fold in Buffer D.

Introduce a 2 µl aliquot of one of the serum samples or ACT standards into each well.

Run for about one hour and ten minutes at 200 V and 400 mA.

Blot any excess liquid off the gel and then finish drying it in an oven set to 37° C.

Stain for one minute with Solution G.

Destain with Solution F until the background is low enough.

Measure the height of the zones of precipitation (rockets) on the gel.

Draw up a standard curve with the concentration of each ACT standard plotted against the height of the corresponding rocket.

Work out the ACT concentration in each of the test samples by reading the value corresponding to the rocket height from the standard curve.

ACT can also be assayed in an ELISA carried out on a microtiter plate. This protocol involves the following steps:

Prepare Buffer H: 0.2 M. tris(hydroxymethyl)-aminomethane, 02 M maleic acid, pH=6.2.

Prepare Solution I: Buffer H supplemented with 5% hydrolyzed casein.

Prepare Buffer J: Buffer H supplemented with 0.5% tween 20.

Prepare Solution K: 0.1 M tris(hydroxymethyl)-aminomethane, 0.1 M NaCl, 1 mM $MgCl_2$, 0.1 mM $ZnCl_2$, 0.9 g/l sodium azide, pH=6.5.

Dilute the anti-ACT antibody (Dako, Reference A022) 1.86-fold in Buffer H.

Introduce 100 µl of the antibody solution into each well on the microtiter plate. Incubate for one hour at 37° C. Aspirate off the solution.

Introduce 200 µl of solution I into each well. Incubate for one hour at 37° C. Aspirate off the solution.

Prepare a set of ACT standards by diluting purified ACT (Scipac, Reference P159-5) in Buffer H.

Dilute the serum samples 500-fold in Buffer H.

Incubate 100 µl aliquots of the samples or standards in each of the wells for one hour at 37° C.

Wash with 3×300 µl of Buffer J.

Dilute the alkaline phosphatase-conjugated anti-ACT (bioMérieux) 500-fold in Solution K.

Incubate a 100 µl aliquot of the conjugate solution in each of the wells for one hour at 37° C.

Wash with 3×300 µl of Buffer J.

Develop with 100 µl of para-Nitro-Phenyl-Phosphate (pNPP) substrate.

Stop the development reaction with 100 µl of 1 M sodium hydroxide.

Read the optical density at 402 nm with subtraction of background noise at 630 nm.

Draw up a standard curve with the concentration of each ACT standard plotted against the corresponding OD reading.

Work out the ACT concentration in each of the test samples by reading the value corresponding to the OD reading from the standard curve.

C—Possible Modifications to the Method

Instead of measuring Total PSA, the amount of PSA-ACT complex can be assayed and the following equation used:

$$\frac{[ACT] \times [PSA-ACT]^2}{[Free\ PSA]}\ (in\ \mu g/ml)^2$$

The patient is diagnosed as having adenocarcinoma of the prostate if this ratio is greater than a first value, and as having benign prostatic hyperplasia if the ratio is below a second value.

It is also possible to use the concentration of PSA-ACT in conjunction with that of Total PSA if the following equation is used:

$$\frac{[ACT] \times [PSA-ACT] \times [Total\ PSA]}{[Free\ PSA]}\ (in\ \mu g/ml)^2$$

Inverting these ratios obviously leads to the same diagnoses as the ratios stipulated in the invention as long as the thresholds are adjusted to take into account the new calculation modalities.

It is of note that this method makes it possible to diagnose case of cancer without using any species that is a tumor marker in the strict sense. This is because both PSA and ACT are expressed to the same extent in normal health individuals as in men with prostate cancer. Diagnosis in this case depends on a combination of a tissue-specific marker (PSA) and a marker for inflammation (ACT). The only marker in current use in this area of oncology is PSA.

Many different tumor markers have been described but none can be used for screening for early-stage disease. The use of these markers is generally limited to establishing a prognosis and therapeutic monitoring. Therefore, the invention demonstrates the value of assaying both a tissue-specific marker and a marker for inflammation in the diagnosis of one type of cancer. A similar approach may be relevant to screening for other forms of cancer, a possibility which would have extremely positive ramifications.

The invention claimed is:

1. A method for diagnosis, in male patients of the adenocarcinoma of the prostate or benign prostatic hyperplasia, comprising:

determining from a serum sample the concentration of at least one tissue-specific marker and the concentration of at least one marker for inflammation, wherein said tissue-specific marker is PSA, and said marker for inflammation is ACT;

determining a ratio based on the combination of the concentration of at least said tissue-specific marker and at least said inflammation marker, said ratio being as follows:

[ACT]×[Total PSA]$^2$/[Free PSA]; and making a diagnosis of adenocarcinoma of the prostate when the ratio is greater than 30 (μg/ml)$^2$ or making a diagnosis of benign prostatic hyperplasia when the ratio is below 16.5 μg/ml)$^2$.

2. The method of claim 1, wherein said ratio is greater than 50 (μg/ml)$^2$ for a diagnosis of adenocarcinoma of the prostate or said ratio is below 12 (μg/ml)$^2$ for a diagnosis of benign prostatic hyperplasia.

3. A method for diagnosis, in male patients of the adenocarcinoma of the prostate or benign prostatic comprising:

determining from a serum sample the concentration of at least one tissue-specific marker and the concentration of at least one marker for inflammation, wherein said tissue-specific marker is PSA, and said marker for inflammation is ACT;

determining a ratio based on the combination of the concentration of at least said tissue-specific marker and at least said inflammation marker, said ratio being as follows:

[ACT]×[PSA-ACT]×[Total PSA]/[Free PSA]; and making a diagnosis of adenocarcinoma of the prostate when the ratio is greater than 23 (μg/ml)$^2$ or making a diagnosis of benign prostatic hyperplasia when the ratio is below 13.5 (μg/ml)$^2$.

4. The method of claim 3, wherein said ratio is greater than 45 (μg/ml)$^2$ for a diagnosis of adenocarcinoma of the prostate or said ratio is below 9 (μg/ml)$^2$ for a diagnosis of benign prostatic hyperplasia.

5. A method for diagnosis, in male patients, of adenocarcinoma of the prostate or benign prostatic hyperplasia, comprising:

determining from a serum sample the concentration of at least one tissue-specific marker and the concentration of at least one marker for inflammation, wherein said tissue-specific marker is PSA, and said marker for inflammation is ACT;

determining a ratio based on the combination of the concentration of at least said tissue-specific marker and at least said inflammation marker, said ratio being as follows:

[ACT]×[PSA-ACT]$^2$ /[Free PSA]; and making a diagnosis of adenocarcinoma of the prostate when the ratio is greater than 17 (μg/ml)$^2$ or making a diagnosis of benign prostatic hyperplasia when the ratio is below 12 (μg/ml)$^2$.

6. The method of claim 5, wherein said ratio is greater than 40 (μg/ml)$^2$ for a diagnosis of adenocarcinoma of the prostate or said ratio is below 7 (μg/ml)$^2$ for a diagnosis of benign prostatic hyperplasia.

* * * * *